(12) United States Patent
Johnston et al.

(10) Patent No.: US 7,820,853 B2
(45) Date of Patent: Oct. 26, 2010

(54) INTEGRATED PROCESS FOR THE PRODUCTION OF VINYL ACETATE FROM ACETIC ACID VIA ETHYL ACETATE

(75) Inventors: Victor J. Johnston, Houston, TX (US); James H. Zink, League City, TX (US); Deborah R. Repman, Lake Jackson, TX (US); Barbara F. Kimmich, League City, TX (US); Josefina T. Chapman, Houston, TX (US); Laiyuan Chen, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 12/319,121

(22) Filed: Dec. 31, 2008

(65) Prior Publication Data

US 2010/0168467 A1    Jul. 1, 2010

(51) Int. Cl.
    *C07C 71/00* (2006.01)
(52) U.S. Cl. .................................................... 560/261
(58) Field of Classification Search ....................... None
    See application file for complete search history.

(56) References Cited

U.S. PATENT DOCUMENTS

| | | | |
|---|---|---|---|
| 2,021,698 A | 11/1935 | Perkins | |
| 2,425,389 A | 8/1947 | Oxley et al. | |
| 2,607,807 A | 8/1952 | Ford | 270/638 |
| 2,859,241 A | 11/1958 | Schnizer | |
| 2,882,244 A | 4/1959 | Milton | 252/455 |
| 3,130,007 A | 4/1964 | Breck | 23/113 |
| 3,702,886 A | 11/1972 | Argauer et al. | 423/328 |
| 4,065,512 A | 12/1977 | Cares | 260/641 |
| 4,270,015 A | 5/1981 | Knifton | 585/324 |
| 4,275,228 A | 6/1981 | Gruffaz | |
| 4,398,039 A | 8/1983 | Pesa et al. | |
| 4,399,305 A | 8/1983 | Schreck | 562/607 |
| 4,443,639 A | 4/1984 | Pesa et al. | |
| 4,517,391 A | 5/1985 | Schuster et al. | 568/885 |
| 4,620,050 A * | 10/1986 | Cognion et al. | 585/640 |
| 4,696,596 A | 9/1987 | Russell | 403/321 |
| 4,777,303 A | 10/1988 | Kitson et al. | |
| 4,804,791 A | 2/1989 | Kitson et al. | |
| 4,826,795 A | 5/1989 | Kitson et al. | |
| 4,843,170 A | 6/1989 | Isshiki et al. | |
| 4,886,905 A | 12/1989 | Larkins, Jr. | |
| 4,978,778 A | 12/1990 | Isshiki et al. | |
| 4,985,572 A | 1/1991 | Kitson et al. | |
| 5,149,680 A * | 9/1992 | Kitson et al. | 502/185 |
| 5,155,084 A | 10/1992 | Horn et al. | |
| 5,185,308 A | 2/1993 | Bartley et al. | 502/170 |
| 5,241,106 A | 8/1993 | Inoue et al. | |
| 5,243,095 A | 9/1993 | Roberts et al. | |
| 5,475,144 A | 12/1995 | Watson et al. | |
| RE35,377 E | 11/1996 | Steinberg et al. | 518/704 |
| 5,674,800 A | 10/1997 | Abel et al. | |
| 5,691,267 A | 11/1997 | Nicolau et al. | 502/330 |
| 5,719,315 A | 2/1998 | Tustin et al. | |
| 5,731,456 A | 3/1998 | Tustin et al. | |
| 5,821,111 A | 10/1998 | Grady et al. | 435/252.5 |
| 6,040,474 A * | 3/2000 | Jobson et al. | 560/243 |
| 6,114,571 A | 9/2000 | Abel et al. | 560/245 |
| 6,232,352 B1 | 5/2001 | Vidalin | 518/700 |
| 6,332,330 B1 | 12/2001 | Loup et al. | |
| 6,476,261 B2 * | 11/2002 | Ellis et al. | 562/606 |
| 6,509,290 B1 | 1/2003 | Vaughn et al. | 502/214 |
| 6,603,038 B1 | 8/2003 | Hagemeyer et al. | 560/241.1 |
| 6,657,078 B2 | 12/2003 | Scates et al. | 562/519 |
| 6,685,754 B2 | 2/2004 | Kindig et al. | 48/210 |
| 6,693,213 B1 | 2/2004 | Kolena et al. | |
| 6,696,596 B1 * | 2/2004 | Herzog et al. | 560/245 |
| 6,727,380 B2 | 4/2004 | Ellis et al. | |
| 6,768,021 B2 | 7/2004 | Horan et al. | |
| 6,812,372 B2 | 11/2004 | Janssen et al. | 585/638 |

(Continued)

FOREIGN PATENT DOCUMENTS

| | | |
|---|---|---|
| EP | 0 330 853 A2 | 9/1989 |
| EP | 0 372 847 A2 | 6/1990 |
| EP | 0372847 * | 6/1990 |
| GB | 1168785 | 10/1969 |
| GB | 1 559 540 | 1/1980 |
| GB | 2 136 704 A | 9/1987 |
| JP | 10-306047 A | 11/1998 |
| JP | 2001-046874 A | 2/2001 |
| JP | 2001-157841 A | 6/2001 |
| WO | WO99/08791 | 2/1999 |
| WO | WO03/040037 | 5/2003 |

OTHER PUBLICATIONS

U.S. Appl. No. 12/221,209, filed Jul. 31, 2008, Johnston et al.

(Continued)

*Primary Examiner*—Karl J Puttlitz

(57) ABSTRACT

This invention provides an integrated three step economical process for the production of vinyl acetate monomer (VAM) from acetic acid in the vapor phase. First, acetic acid is selectively hydrogenated over a hydrogenating catalyst composition to form ethyl acetate which is cracked to form ethylene and acetic acid in the second step and in a subsequent step so formed ethylene and acetic acid is reacted with molecular oxygen over a suitable catalyst to form VAM. In an embodiment of this invention reaction of acetic acid and hydrogen over platinum and copper supported on silica selectively produces ethyl acetate in a vapor phase at a temperature of about 250° C., which is cracked over a NAFION catalyst to form ethylene and acetic acid at a temperature of about 185° C., which is mixed with molecular oxygen and reacted over a palladium/gold/potassium catalyst supported on titania to form VAM at a temperature of about 150° C. to 170° C.

26 Claims, No Drawings

U.S. PATENT DOCUMENTS

| | | | |
|---|---|---|---|
| 6,852,877 | B1 | 2/2005 | Zeyss et al. ............ 560/241 |
| 2003/0013908 | A1 | 1/2003 | Horan et al. |
| 2006/0019360 | A1 | 1/2006 | Verser et al. |
| 2006/0106246 | A1* | 5/2006 | Warner et al. ............ 560/241 |
| 2009/0005588 | A1 | 1/2009 | Hassan et al. |
| 2010/0029980 | A1 | 2/2010 | Johnston et al. |
| 2010/0121114 | A1 | 5/2010 | Weiner et al. |

OTHER PUBLICATIONS

Brunauer Emmett and Teller J. Am. Chem. Soc. 60,309 (1938); Proc. Roy. Soc. A314, pp. 473-498; Mol. Sieves Pap. Conf., 1967, 78, Soc. Chem. Ind. London, by D. Domine and J. Quobex; Malinowski et al., Bull. Soc. Chim. Belg. (1985), 94(2), 93-5.

Loessard et al., Studies in Surface Science and Catalysis (1989), Volume Date 1988, 48 (Struct. React. Surf.), 591-600; Hindermann et al., J. Chem. Res., Synopses (1980), (11), 373; DePuy and King, Chem. Rev., 60, 431-445 (1960); and duPont "Innovation," vol. 4, No. 3, Spring 1973.

International Search Report and Written Opinion for PCT/US2009/004197 mailed Mar. 24, 2010 (14 pages).

International Search Report and Written Opinion for PCT/US2009/004195 mailed Mar. 26, 2010 (12 pages).

Pallassana et al., Reaction Paths in the Hydrogenolysis of Acetic Acid to Ethanol over Pd(111), Re(0001), and PdRe Alloys. Journal of Catalysis 209:289-305 (2002).

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

Tustin et al. Synthesis of vinyl acetate monomer from synthesis gas, Catalyst Today, vol. 58(4) (2000) pp. 281-291.

Santori et al. (2000). Hydrogenation of carbonylic compounds on Pt/SiO2 catalysts modified with SnBu4, Studies in Surface Science and Catalysis, 130, 2063-2068.

Roscher, "Ullmann's Encyclopedia of Industrial Chemistry—Vinyl Esters," Ullmann's Encyclopedia of Industrial Chemistry (2000) p. 1-18.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

* cited by examiner

INTEGRATED PROCESS FOR THE PRODUCTION OF VINYL ACETATE FROM ACETIC ACID VIA ETHYL ACETATE

FIELD OF THE INVENTION

The present invention relates generally to an integrated process for the production of vinyl acetate monomer (VAM) from acetic acid via ethyl acetate. More specifically, the present invention relates to an integrated process first involving hydrogenating acetic acid utilizing a catalyst composed of a supported bimetal catalyst, such as for example, platinum or palladium and copper or cobalt supported on a suitable catalyst support optionally containing one or more additional hydrogenating metals to form ethyl acetate with high selectivity. In a subsequent second step, ethyl acetate thus formed is subjected to a pyrolysis step to form ethylene and in a final step the thus formed ethylene is combined with additional amounts of acetic acid and molecular oxygen to form vinyl acetate over a suitable catalyst.

BACKGROUND

There is a long felt need for an economically viable process to form VAM directly from acetic acid. VAM is an important monomer in the production of polyvinyl acetate and polyvinyl alcohol products among other important uses. VAM is currently produced from two key raw materials, ethylene and acetic acid. Ethylene is predominantly produced from petroleum based raw materials although acetic acid can be produced to a lesser extent from petroleum based raw materials. Therefore, fluctuating natural gas and crude oil prices contribute to fluctuations in the cost of conventionally produced petroleum or natural gas-sourced VAM, making the need for alternative sources of VAM all the greater when oil prices rise.

It has now been found that VAM can be produced essentially from a mixture of carbon monoxide and hydrogen (commonly known as synthesis gas) involving a few industrially viable steps. For example, it is well know that synthesis gas can be reduced to methanol, which is in fact the industrially preferred way to manufacture methanol. Methanol thus formed can then be converted selectively to acetic acid under catalytic carbonylation conditions which is again the industrially preferred process for the manufacture of acetic acid. The acetic acid thus formed then can be selectively converted to ethyl acetate under suitable catalytic conditions. Although there are no known preferred processes for such a conversion, the prior art does provide certain processes for such a conversion of acetic acid to ethyl acetate albeit at low conversions and yields thus making it industrially unsuitable.

For instance, one such process involves first hydrogenation of carboxylic acids over heterogeneous catalysts to produce alcohols, which can then be converted to the corresponding acetates by an esterification reaction. For example, U.S. Pat. No. 2,607,807 to Ford discloses that ethanol can be formed from acetic acid over a ruthenium catalyst at extremely high pressures of 700-950 bar in order to achieve yields of around 88%, whereas low yields of only about 40% are obtained at pressures of about 200 bar. However such extreme reaction conditions are unacceptable and uneconomical for a commercial operation.

More recently, even though it may not still be commercially viable it has been reported that ethanol can be produced from hydrogenating acetic acid using a cobalt catalyst at superatmospheric pressures such as about 40 to 120 bar. See, for example, U.S. Pat. No. 4,517,391 to Shuster et al.

On the other hand, U.S. Pat. No. 5,149,680 to Kitson et al. describes a process for the catalytic hydrogenation of carboxylic acids and their anhydrides to alcohols and/or esters utilizing a platinum group metal alloy catalyst. The catalyst is comprised of an alloy of at least one noble metal of Group VIII of the Periodic Table and at least one metal capable of alloying with the Group VIII noble metal, admixed with a component comprising at least one of the metals rhenium, tungsten or molybdenum. Although it has been claimed therein that improved selectivity to a mixture of alcohol and its ester with the unreacted carboxylic acid is achieved over the prior art references it was still reported that 3 to 9 percent of alkanes, such as methane and ethane are formed as by-products during the hydrogenation of acetic acid to ethanol under their optimal catalyst conditions.

A slightly modified process for the preparation of ethyl acetate by hydrogenating acetic acid has been reported in EP 0 372 847. In this process, a carboxylic acid ester, such as for example, ethyl acetate is produced at a selectivity of greater than 50% while producing the corresponding alcohol at a selectivity less than 10% from a carboxylic acid or anhydride thereof by reacting the acid or anhydride with hydrogen at elevated temperature in the presence of a catalyst composition comprising as a first component at least one of Group VIII noble metal and a second component comprising at least one of molybdenum, tungsten and rhenium and a third component comprising an oxide of a Group IVb element. However, even the optimal conditions reported therein result in significant amounts of by-products including methane, ethane, acetaldehyde and acetone in addition to ethanol. In addition, the conversion of acetic acid is generally low and is in the range of about 5 to 40% except for a few cases in which the conversion reached as high as 80%.

Similarly, it has been reported in the literature that ethyl acetate can be converted to ethylene under a variety of conditions. Although some of the processes reported in the art may not be suitable for a commercial operation, certain modifications thereof maybe suitable for selective conversion of ethyl acetate to ethylene such that it can be employed industrially as further described herein in the detailed description of the instant invention.

For example, it has been reported that ethylene can be produced from various ethyl esters in the gas phase in the temperature range of 150-300° C. over zeolite catalysts. The types of ethyl esters that can be employed include ethyl esters of formic acid, acetic acid and propionic acid. See, for example, U.S. Pat. No. 4,620,050 to Cognion et al., where selectivity is reported to be acceptable.

U.S. Pat. No. 4,270,015 to Knifton describes obtaining ethylene involving a two-step process in which a mixture of carbon monoxide and hydrogen is reacted with a carboxylic acid containing 2 to 4 carbon atoms to form the corresponding ethyl ester of said carboxylic acid which is subsequently pyrolyzed in a quartz reactor at elevated temperatures in the range of about 200° to 600° C. to obtain ethylene. The ethylene thus produced contains other hydrocarbons, particularly, ethane as an impurity. It was also reported therein that the concentration of ethane can reach high values, near 5% by pyrolyzing pure ethyl propionate at 460° C. More importantly, the conversion of the esters and yield of ethylene are reported to be very low.

U.S. Pat. No. 4,399,305 to Schreck describes obtaining high purity ethylene from ethyl acetate employing a cracking catalyst composed of a perfluorosulfonic acid resin commercially sold under the trademark NAFION® by E.I. DuPont de Nemours & Co.

On the other hand, Malinowski et al., *Bull. Soc. Chim. Belg.* (1985), 94(2), 93-5, disclose the reaction of acetic acid on low-valent titanium heterogenized on support materials such as silica ($SiO_2$) or titania ($TiO_2$) resulted in a mixture of products including diethyl ether, ethylene and methane where selectivity is poor.

WO 2003/040037 discloses that crystalline microporous metalloalumino-phosphates (ELAPO), particularly, SAPO-type zeolites, such as SAPO-5, SAPO-11, SAPO-20, SAPO-18 and SAPO-34, having Si/Al ratio of 0.03-017 are useful as adsorbent or as a catalyst for the production of olefins from an oxygenated feedstock containing methanol, ethanol, n-propanol, isopropanol, C4-C20 alcohols, methyl ethyl ether, dimethyl ether, di-ethyl ether, di-isopropyl ether, formaldehyde, dimethyl carbonate, dimethyl ketone and/or acetic acid. A similar disclosure utilizes a silicoaluminophosphate molecular sieves comprising at least one intergrown phase of molecular sieve. It is reported that in this process a feedstock containing an oxygenate contacts a catalyst comprising the molecular sieve in a reaction zone of a reactor at conditions effective to produce light olefins, particularly ethylene and propylene. See U.S. Pat. No. 6,812,372 to Janssen et al. It is mentioned that such oxygenated feedstocks include acetic acid, but the disclosure appears to be limited to either methanol or dimethyl ether. See, also, U.S. Pat. No. 6,509,290 to Vaughn et al., which further discloses conversion of oxygenated feedstocks to olefins.

Bimetallic ruthenium-tin/silica catalysts have been prepared by reaction of tetrabutyl tin with ruthenium dioxide supported on silica. It has been reported that these catalysts exhibit different selectivities based on their content of tin/ruthenium ratio (Sn/Ru). Specifically, it has been reported that the selectivity for the hydrogenolysis of ethyl acetate is quite different, which depends upon the Sn/Ru ratio in the catalyst. For instance, with ruthenium alone on $SiO_2$, the reaction is not selective: methane, ethane, carbon monoxide, carbon dioxide as well as ethanol and acetic acid are produced. Whereas, with low tin content, it has been reported that the catalysts are fairly selective for the formation of acetic acid, while at higher Sn/Ru ratios, ethanol is the only detected product. See Loessard et al., *Studies in Surface Science and Catalysis* (1989), Volume Date 1988, 48 (Struct. React. Surf.), 591-600.

The catalytic reduction of acetic acid has also been studied. For instance, Hindermann et al., *J. Chem. Res. Synopses* (1980), (11), 373, have disclosed the catalytic reduction of acetic acid on iron and on alkali-promoted iron. In their study they found that the reduction of acetic acid on alkali-promoted iron, followed at least two different routes depending on the temperature. For example, they found that at 350° C., the Piria reaction was predominant and gave acetone and carbon dioxide, as well as the decomposition products methane and carbon dioxide, whereas the decomposition products were reduced at lower temperatures. On the other hand, at 300° C. a normal reduction reaction was observed resulting in the formation of acetaldehyde and ethanol.

In addition, it should also be noted that there are industrially viable processes for the production of VAM from ethylene and acetic acid. For example, U.S. Pat. No. 6,696,596 to Herzog et al., which is incorporated herein by reference in its entirety, discloses that VAM can be produced in the gas phase from ethylene, acetic acid and oxygen or oxygen containing gases over a catalyst comprising palladium and/or its compounds, gold and/or its compounds and alkali metal compounds on a support, wherein the catalyst further comprises vanadium and/or its compounds.

There are also reports in the literature of integrated processes for the manufacture of VAM involving oxidation of an alkane such as ethane or an alkene such as ethylene to acetic acid and in a subsequent step reaction of so formed acetic acid with additional amounts of ethylene in the presence of oxygen to form VAM. See for instance, U.S. Pat. No. 6,040,474 to Jobson et al., which describes the manufacture of acetic acid and/or vinyl acetate using two reaction zones wherein the first reaction zone comprises ethylene and/or ethane for oxidation to acetic acid with the second reaction zone comprising acetic acid and ethylene with the product streams being subsequently separated thereby producing vinyl acetate. See also, U.S. Pat. No. 6,476,261 to Ellis et al. which describes an oxidation process for the production of alkenes and carboxylic acids such as ethylene and acetic acid which are reacted to form vinyl acetate demonstrating that more than one reaction zone can be used to form the vinyl acetate.

U.S. Pat. No. 6,852,877 to Zeyss et al., describes another integrated process wherein ethane is reacted with molecular oxygen in the presence of a suitable oxidation catalyst in first reaction zone; concurrently, in a second reaction zone another batch of ethane is oxidatively dehydrogenated to ethylene in the presence of a suitable catalyst and subsequently in a third reaction zone, the acetic acid formed in reaction zone 1 is reacted with ethylene produced from a second reaction zone in the presence of additional amounts of molecular oxygen and a suitable catalyst to form VAM.

From the foregoing it is apparent that existing processes do not have the requisite selectivity to form ethyl acetate from acetic acid and/or its direct conversion to ethylene and then to convert the resulting products to VAM in an integrated process thus making them industrially adoptable to produce VAM essentially from synthesis gas and/or synthesis gas based products.

SUMMARY OF THE INVENTION

Surprisingly, it has now been unexpectedly found that VAM can be produced on an industrial scale involving an integrated process by which ethyl acetate is first formed directly from acetic acid with very high selectivity and yield, which is subsequently pyrolyzed to form ethylene and acetic acid. In a final step the mixture of ethylene and acetic acid so formed in second step is mixed with molecular oxygen and optionally with more acetic acid to form VAM in the presence of a suitable catalyst. More particularly, this invention provides a process for the selective formation of VAM from acetic acid comprising: (a) hydrogenating acetic acid in the first reaction zone in the presence of hydrogen over a hydrogenating catalyst comprising at least one metal selected from the group consisting of nickel, platinum and palladium and at least one metal selected from molybdenum, rhenium, zirconium, copper and cobalt with the proviso that platinum may be used without molybdenum, rhenium, zirconium, copper or cobalt to produce a first gaseous product stream; (b) enriching said first gaseous product stream with ethyl acetate at least up to 50 mole percent; (c) reacting said enriched first gaseous product stream from step (b) over a suitable cracking catalyst in a second reaction zone to form a second gaseous product stream consisting essentially of ethylene and acetic acid; (d) reacting said second gaseous product stream from step (c) with molecular oxygen and optionally additional amounts of acetic acid in the presence of a catalyst to form a third gaseous product stream comprising vinyl acetate; and (e) separating the vinyl acetate from said third gaseous product stream.

In addition, the catalyst employed in step (a) is comprised of a suitable catalyst support optionally including one or more metal catalysts selected from the group consisting of ruthenium, iridium, chromium, tin, tungsten, vanadium and zinc. More specifically, the catalyst suitable for the process of step (a) of this invention is typically comprised of a combination of platinum and copper supported on a suitable catalyst support or palladium and cobalt supported on a suitable catalyst support. Suitable catalyst supports include without any limitation, silica, alumina, calcium silicate, carbon, zirconia, zirconia-silica, titania, titania-silica, iron oxide and zeolite catalysts such as, for example, H-ZSM-5. Similarly, various supports as described herein may also be employed in steps (c) and (d) of this invention.

DETAILED DESCRIPTION OF THE INVENTION

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. Mole percent (mole % or %) and like terms refer to mole percent unless otherwise indicated. Weight percent (wt % or %) and like terms refer to weight percent unless otherwise indicated.

Typically, the catalyst metal loadings are expressed as weight percent of a catalyst metal based on the total dry weight of the metal and catalyst support. Thus, for example, one (1) weight percent of metal on a support means that one gram of pure metal is present in 100 grams of supported metal catalyst, i.e., the combined weight of support (99 grams) and the metal (1 gram).

"Conversion" is expressed as a mole percentage based on acetic acid in the feed. The conversion of acetic acid (AcOH) is calculated from gas chromatography (GC) data using the following equation:

$$\text{AcOH conversion}(\%) = 100 * \frac{\text{mmol AcOH in (feed stream)} - \text{mmol AcOH out } (GC)}{\text{mmol AcOH in (feed stream)}}$$

"Selectivity" is expressed as a mole percent based on converted acetic acid. For example, if the conversion is 50 mole % and 50 mole % of the converted acetic acid is converted to ethyl acetate (EtOAC), we refer to the ethyl acetate selectivity as 50%. Selectivity is calculated from gas chromatography (GC) data using the following equation:

$$\text{Selectivity to EtOAc} = 100 * \frac{\text{mmol EtOAc out } (GC)}{\frac{\text{Total mmol C out } (GC)}{2} - \text{mmol AcOH out } (GC)}$$

wherein "Total mmol C out (GC)" refers to total mmols of carbon from all of the products analyzed by gas chromatograph.

The reaction proceeds in accordance with the following chemical equations:

(a) Hydrogenation of Acetic Acid to Ethyl Acetate

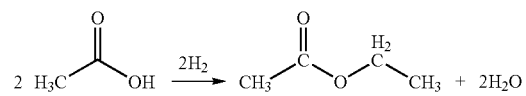

(b) Cracking of Ethyl Acetate to Ethylene and Acetic Acid

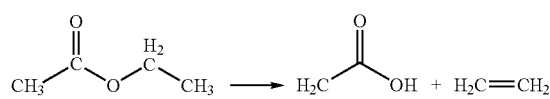

(c) Oxidative Addition of Acetic Acid to Ethylene to form VAM

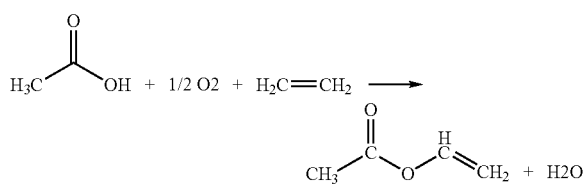

Step (a): Hydrogenation of Acetic Acid to Ethyl Acetate

In accordance with the invention, conversion of acetic acid to ethyl acetate can be carried out in a variety of configurations, such as for example in a single reaction zone which may be a layered fixed bed, if so desired. An adiabatic reactor could be used, or a shell and tube reactor provided with a heat transfer medium could be used. The fixed bed can comprise a mixture of different catalyst particles or catalyst particles which include multiple catalysts as further described herein. The fixed bed may also include a layer of particulate material making up a mixing zone for the reactants. A reaction mixture including acetic acid, hydrogen and optionally an inert carrier gas is fed to the bed as a stream under pressure to the mixing zone. The stream is subsequently supplied (by way of pressure drop) to the reaction zone or layer. Reaction zone comprises a catalytic composition including a suitable hydrogenating catalyst where acetic acid is hydrogenated to produce ethyl acetate. Any suitable particle size may be used depending upon the type of reactor, throughput requirements and so forth.

Although various metal supported hydrogenating catalysts known to one skilled in the art can be employed in hydrogenating acetic acid to form ethyl acetate in step (a) of the process of this invention, it is preferred that the hydrogenating catalyst employed is comprised of at least one metal selected from the group consisting of nickel, platinum and palladium and at least one metal selected from molybdenum, rhenium, zirconium, copper and cobalt. In addition, the catalyst is comprised of a suitable catalyst support optionally including one or more metal catalysts selected from the group consisting of ruthenium, iridium, chromium, tin, tungsten, vanadium and zinc. However, single supported metal catalyst such as platinum alone supported on a suitable catalyst support such as titania may also be employed in the process of this invention.

Preferably, the catalyst suitable for the process of this invention is comprised of a combination of platinum and copper supported on a suitable catalyst support or palladium and cobalt supported on a suitable catalyst support. Typically, it is preferred that a suitable weight ratio of a combination of metals on a suitable support can be used as a hydrogenating catalyst. Thus, for example, a combination of platinum and copper (Pt/Cu) or palladium and cobalt (Pd/Co) in the weight ratio of about 0.1-1 are particularly preferred. More preferably, a weight ratio of Pt/Cu or Pd/Co is about 0.2-0.5 and most preferably the weight ratio of Pt/Cu or Pd/Co is about 0.2.

The other catalysts suitable in the process of this invention include a bimetallic combination of nickel/molybdenum (Ni/Mo), palladium/molybdenum (Pd/Mo) or platinum/molybdenum (Pt/Mo) supported on H-ZSM-5, silica or carbon. In this aspect of the invention the loading levels of a bimetallic combination of Ni/Mo may be any level to affect the selective hydrogenation of acetic acid to ethyl acetate and typically it is about 1 weight percent nickel and 5 weight percent molybdenum (1 wt % Ni/5 wt % Mo) supported on carbon.

In another aspect, the loading levels of a bimetallic combination of Pd/Mo is about 1 weight percent palladium and 5 weight percent molybdenum (1 wt % Pd/5 wt % Mo) supported on H-ZSM-5 or silica. Similarly, a bimetallic combination of Pt/Mo with a loading of about 1 weight percent platinum and 5 weight percent molybdenum (1 wt % Pt/5 wt % Mo) supported on silica or carbon can also be employed.

In another aspect of this invention, the catalyst is chosen from a bimetallic combination of nickel/rhenium (Ni/Re) or palladium/rhenium (Pd/Re) supported on titania. Again, in this aspect of the invention any suitable metal loadings can be employed to bring about the selective hydrogenation of acetic acid to ethyl acetate. For instance a bimetallic combination of 1 weight percent nickel and 5 weight percent rhenium (1 wt % Ni/5 wt % Re) supported on titania or a bimetallic combination of 1 weight percent palladium and 5 weight percent rhenium (1 wt % Pd/5 wt % Re) supported on titania can be employed.

In another embodiment of this invention, there is also provided a process for selective and direct formation of ethyl acetate from acetic acid comprising: contacting a feed stream containing acetic acid and hydrogen at an elevated temperature with a suitable hydrogenating catalyst containing about 0.5 weight percent to about 1 weight percent of palladium and 2.5 weight percent to about 5 weight percent of rhenium on a suitable catalyst support. More specifically, the catalyst support contains palladium at a loading level of about one (1) weight percent and rhenium at a loading level of about five (5) weight percent and the catalyst support is titania.

In this aspect of the invention, the reactants consist of acetic acid and hydrogen with a molar ratio in the range of about 1:10 to 1:5, the temperature of the reaction zone is in the range of about 225° C. to 275° C., and the pressure of the reaction zone is in the range of about 10 to 20 atmospheres absolute.

Various catalyst supports known in the art can be used to support the catalysts of this invention. Examples of such supports include without any limitation, zeolite, such as H-ZSM-5, iron oxide, silica, alumina, titania, zirconia, magnesium oxide, calcium silicate, carbon, graphite and a mixture thereof. Preferred supports are silica, alumina, calcium silicate, carbon, zirconia and titania. More preferably silica is used as a catalyst support in the process of this invention. It is also important to note that higher the purity of silica, the better it functions as a support.

In another aspect of the process of this invention, any of known zeolite catalysts can also be employed as a catalyst support. While any zeolite having a pore diameter of at least about 0.6 nm can be used, preferably employed among such zeolites are the catalyst supports selected from the group consisting of mordenites, ZSM-5, a zeolite X and a zeolite Y.

The preparation of large-pore mordenites is described, for example, in U.S. Pat. No. 4,018,514 to Plummer and in Mol. Sieves Pap. Conf., 1967, 78, Soc. Chem. Ind. London, by D. DOMINE and J. QUOBEX.

Zeolite X is described, for example, in U.S. Pat. No. 2,882,244 to Milton and zeolite Y in U.S. Pat. No. 3,130,007 to Breck.

Various zeolites and zeolite-type materials are known in the art for the catalysis of chemical reactions. For example, U.S. Pat. No. 3,702,886, to Argauer, discloses a class of synthetic zeolites, characterized as "Zeolite ZSM-5", which are effective for the catalysis of various hydrocarbon conversion processes.

The zeolites suitable for the procedure of the invention can be in the basic form, in the partially or totally acidified form, or in the partially dealuminated form.

Preferably, the zeolite catalyst support in the process of the present invention are in the protic form, characterized as "H-ZSM-5" or "H-mordenite" zeolites, which are prepared from a corresponding "ZSM-5" zeolite or "mordenite" zeolite by replacing most, and generally at least about 80% of the cations of the latter zeolite with hydrogen ions using techniques well-known in the art. These zeolite catalysts are essentially crystalline aluminosilicates or in the neutral form a combination of silica and alumina in a well defined crystalline structure. In a particularly preferred class of zeolite catalysts for purposes of the present invention, the molar ratio of $SiO_2$ to $Al_2O_3$ in these zeolites is within the ratio of about 10 to 60.

In another aspect of this invention, the combination of catalyst metals, palladium and cobalt or a combination of platinum and copper are supported on a high purity low surface area silica or H-ZSM-5 using the procedures well known in the art or the procedures further described herein. Other preferred catalyst supports for platinum or palladium based metal catalysts are carbon, titania and zirconia.

In another embodiment of this invention, the preferred catalyst support is carbon. Various forms of carbon known in the art that are suitable as catalyst support can be used in the process of this invention. Particularly preferred carbon support is a graphitized carbon, particularly the high surface area graphitized carbon as described in Great Britain Patent No. 2,136,704. The carbon is preferably in particulate form, for example, as pellets. The size of the carbon particles will depend on the pressure drop acceptable in any given reactor (which gives a minimum pellet size) and reactant diffusion constraint within the pellet (which gives a maximum pellet size).

The carbon catalyst supports that are suitable in the process of this invention are preferably porous carbon catalyst supports. With the preferred particle sizes the carbon will need to be porous to meet the preferred surface area characteristics.

The catalyst supports, including the carbon catalyst supports, may be characterized by their BET, basal plane, and edge surface areas. The BET surface area is the surface area determined by nitrogen adsorption using the method of Brunauer Emmett and Teller, *J. Am. Chem. Soc.*, 60,309 (1938). The basal plane surface area is the surface area determined from the heat of adsorption on the carbon of n-dotriacontane from n-heptane by the method described in *Proc. Roy. Soc.* A314 pages 473-498, with particular reference to page 489. The edge surface area is the surface area determined from the heat of adsorption on the carbon of n-butanol from n-heptane as disclosed in the *Proc. Roy. Soc.* article mentioned above with particular reference to page 495.

The preferred carbon catalyst supports for use in the present invention have a BET surface area of at least 100 m$^2$/g, more preferably at least 200 m$^2$/g, most preferably at least 300 m$^2$/g. The BET surface area is preferably not greater than 1000 m$^2$/g, more preferably not greater than 750 m$^2$/g.

It is possible to use carbon catalyst supports with ratios of basal plane surface area to edge surface area of at least 10:1, preferably at least 100:1. It is not believed that there is an upper limit on the ratio, although in practice it will not usually exceed 200:1.

The preferred carbon support may be prepared by heat treating a carbon-containing starting material. The starting material may be an oleophillic graphite e.g. prepared as disclosed in Great Britain Patent No. 1,168,785 or may be a carbon black.

However, oleophillic graphites contain carbon in the form of very fine particles in flake form and are therefore not very suitable materials for use as catalyst supports. We prefer to avoid their use. Similar considerations apply to carbon blacks which also have a very fine particle size.

The preferred materials are activated carbons derived from vegetable materials, e.g. coconut charcoal, or from peat or coal or from carbonizable polymers. The materials subjected to the heat treatment preferably have particle sizes not less than these indicated above as being preferred for the carbon support.

The preferred starting materials have the following characteristics: BET surface area of at least 100 m$^2$/g, more preferably at least 500 m$^2$/g.

One preferred heat treatment procedure for preparing carbon supports having the defined characteristics, comprise successively (1) heating the carbon in an inert atmosphere at a temperature of from 900° C. to 3300° C., (2) oxidizing the carbon at a temperature between 300° C. and 1200° C., (3) heating in an inert atmosphere at a temperature of between 900° C. and 3000° C.

The oxidation step is preferably carried out at temperatures between 300° and 600° C. when oxygen (e.g. as air) is used as the oxidizing agent.

The duration of the heating in inert gas is not critical. The time needed to heat the carbon to the required maximum temperature is sufficient to produce the required changes in the carbon.

The oxidation step must clearly not be carried out under conditions such that the carbon combusts completely. It is preferably carried out using a gaseous oxidizing agent fed at a controlled rate to avoid over-oxidation. Examples of gaseous oxidizing agents are steam, carbon dioxide, and gases containing molecular oxygen, e.g. air. The oxidation is preferably carried out to give a carbon weight loss of at least 10 weight percent based on the weight of carbon subjected to the oxidation step, more preferably at least 15 weight percent.

The weight loss is preferably not greater than 40 weight percent of the carbon subjected to the oxidation step, more preferably not greater than 25 weight percent of the carbon.

The rate of supply of oxidizing agent is preferably such that the desired weight loss takes place over at least 2 hours, more preferably at least 4 hours.

Where an inert atmosphere is required it may be supplied by nitrogen or an inert gas.

As noted above, the loading levels of a combination of two metal catalysts are generally referenced with the content of main catalyst metal and the weight ratio of the combination. For instance, the weight ratio of Pt/Cu or Pd/Co is in the range of about 0.1 to 2. Thus, when the weight ratio of Pt/Cu or Pd/Co is 0.1, the amount of platinum or palladium can be 0.1 or 1 weight percent and thus 1 or 10 weight percent of copper or cobalt is present on the catalyst support. More preferably, the weight ratio of Pt/Cu or Pd/Co is about 0.5, and thus the amount of platinum or palladium on the catalyst support can be either 0.5 or 1 weight percent and that of copper or cobalt is either one or two weight percent. More preferably, the weight ratio of Pt/Cu or Pd/Co is one or 0.2. Thus the amount of platinum or palladium on a support is 0.5, one or two weight percent and that of copper or cobalt is also 0.5, one or two weight percent when the weight ratio is one. Similarly, when a weight ratio of Pt/Cu or Pd/Co is 0.2, the amount of platinum or palladium on the support can be 0.5 or one weight percent and of copper or cobalt is either 2.5 or five weight percent.

The amount of third metal loading if present on a support is not very critical in this invention and can vary in the range of about 0.1 weight percent to about 10 weight percent. A metal loading of about 1 weight percent to about 6 weight percent based on the weight of the support is particularly preferred.

The metal impregnation can be carried out using any of the known methods in the art. Typically, before impregnation the supports are dried at 120° C. and shaped to particles having size distribution in the range of about 0.2 to 0.4 mm. Optionally the supports may be pressed, crushed and sieved to a desired size distribution. Any of the known methods to shape the support materials into desired size distribution can be employed.

For supports having low surface area, such as, for example, alpha-alumina, the metal solutions are added in excess until complete wetness or excess liquid impregnation so as to obtain desirable metal loadings.

As noted above, the hydrogenation catalysts used in the process of this invention are at least bimetallic containing platinum/copper, palladium/cobalt and so on. Generally, without intending to be bound by any theory, it is believed that one metal acts as a promoter metal and another metal is the main metal. For instance, in the instant process of the invention, of the above noted combinations respectively platinum, palladium, and copper are considered as main metals for preparing hydrogenation catalysts of this invention. The other metals, copper with platinum, cobalt with palladium are considered to be the promoter metals depending upon various reaction parameters including, but not limited to, catalyst support employed, reaction temperature and pressure, etc. The catalysts may include other promoter metals, such as tungsten, vanadium, molybdenum, chromium or zinc.

The bimetallic catalysts are generally impregnated in two steps. Each impregnation step is followed by drying and calcination. The bimetallic catalysts may also be prepared by co-impregnation. In most cases, the impregnation may be carried out using metal nitrate solutions. However, various other soluble salts which upon calcination release metal ions can also be used. Examples of other suitable metal salts for impregnation include metal oxalate, metal hydroxide, metal oxide, metal acetate, ammonium metal oxide, such as ammonium heptamolybdate hexahydrate, metal acids, such as perrhenic acid solution, and the like.

Thus in one embodiment of this invention, there is provided a hydrogenation catalyst wherein the catalyst support is silica with a bimetallic loading of platinum and copper. In this aspect of the invention, the loading of platinum is about 0.5 weight percent to about 1 weight percent and the loading of copper is about 2.5 weight percent to about 5 weight percent. Specifically, platinum/copper loading levels of 1/1, 1/5, 0.5/0.5, and 0.5/2.5 weight percent on silica can be used.

In another embodiment of this invention, there is further provided a hydrogenation catalyst wherein the catalyst support is high purity low surface area silica with a bimetallic loading of platinum and copper or palladium and cobalt. In this aspect of the invention, the loading of platinum or palladium is about 0.5 weight percent to about 1 weight percent and the loading of copper or cobalt is about 0.1 weight percent to about 5 weight percent. Specifically, platinum/copper or palladium/cobalt loading levels of 1/1, 1/5, 0.5/0.5, and 0.5/2.5 weight percent on high purity low surface area silica can be used. Other preferred supports in this aspect of the invention include H-ZSM-5, graphitized carbon, zirconia, titania, iron oxide, silica-alumina and calcium silicate.

In a further embodiment of this invention, there is provided a hydrogenation catalyst wherein the bimetallic catalyst is copper and chromium supported on silica, zirconia, graphitized carbon, H-ZSM-5, titania-silica and zirconia-silica. In this aspect of the invention, the loading level of copper and chromium is about 3 weight percent to about 10 weight percent each. Specifically, copper/chromium loading levels of 5 weight percent each on any of the aforementioned catalyst support is preferred.

In general, by the practice of this invention, acetic acid can selectively be converted to ethyl acetate at very high rates. The selectivity to ethyl acetate in general is very high and may be at least 60 percent. Under preferred reaction conditions, acetic acid is selectively converted to ethyl acetate at a selectivity of greater than 85 or 87.5 percent or more preferably at a selectivity of 90 percent or more. Most preferably ethyl acetate selectivity is at least 95 percent.

The conversion of acetic acid using the catalysts of this invention is at least 20% and can be up to 70% with selectivity to ethyl acetate at least 60%, preferably 80% and most preferably 95%.

Generally, the active catalysts of the invention are the single metal or the bimetallic catalysts as described herein. More specifically, a bimetallic catalyst containing platinum and copper supported on silica with a platinum loading of 1 weight percent and copper loading of 5 weight percent is preferred. In accordance with the practice of this invention, acetic acid can be converted using this catalyst at conversions of around 70% with ethyl acetate selectivity of at least 80%, more preferably selectivity to ethyl acetate of at least 90% can be achieved.

Similar conversions and selectivities are achieved using zirconia, graphite or titania as a support and with loadings of platinum and copper of one weight percent and five weight percent respectively. Other promoter metals can also be used in conjunction with palladium or platinum as noted above.

In another aspect of this invention, it is also possible to obtain high levels of conversions in the order of at least 25% and high selectivity to ethyl acetate of at least about 90% using palladium loading of one weight percent and cobalt loading of five weight percent on silica or H-ZSM-5 as catalyst supports. In this aspect of the invention, other preferred catalyst supports include graphitized carbon, titania, zirconia, iron oxide, silica-alumina and calcium silicate.

In another aspect of the process of this invention, the hydrogenation is carried out at a pressure just sufficient to overcome the pressure drop across the catalytic bed.

The reaction may be carried out in the vapor or liquid state under a wide variety of conditions. Preferably, the reaction is carried out in the vapor phase. Reaction temperatures may be employed, for example in the range of about 200° C. to about 300° C., preferably about 225° C. to about 275° C. The pressure is generally uncritical to the reaction and subatmospheric, atmospheric or superatmospheric pressures may be employed. In most cases, however, the pressure of the reaction will be in the range of about 5 to 30 atmospheres absolute, most preferably the pressure of reaction zone is in the range of about 8 to 20 atmospheres absolute.

Although the reaction consumes a mole of hydrogen per mole of acetic acid to produce a ½ mole of ethyl acetate, the actual molar ratio of acetic acid to hydrogen in the feed stream may be varied between wide limits, e.g. from about 100:1 to 1:100. It is preferred however that such ratio be in the range of about 1:20 to 1:2. More preferably the molar ratio of acetic acid to hydrogen is about 1:5.

The raw materials used in connection with the process of this invention may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation and so forth. As petroleum and natural gas have become more expensive, methods for producing acetic acid and intermediates such as methanol and carbon monoxide from alternate carbon sources have drawn more interest. Of particular interest is the production of acetic acid from synthesis gas (syngas) that may be derived from any suitable carbon source. U.S. Pat. No. 6,232,352 to Vidalin, the disclosure of which is incorporated herein by reference, for example teaches a method of retrofitting a methanol plant for the manufacture of acetic acid. By retrofitting a methanol plant the large capital costs associated with CO generation for a new acetic acid plant are significantly reduced or largely eliminated. All or part of the syngas is diverted from the methanol synthesis loop and supplied to a separator unit to recover CO and hydrogen, which are then used to produce acetic acid. In addition to acetic acid, the process can also be used to make hydrogen which is utilized in connection with this invention.

U.S. Pat. No. RE 35,377 to Steinberg et al., also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolyzed with additional natural gas to form synthesis gas. The syngas is converted to methanol which may be carbonylated to acetic acid. The method likewise produces hydrogen which may be used in connection with this invention as noted above. See also, U.S. Pat. No. 5,821,111 to Grady et al., which discloses a process for converting waste biomass through gasification into synthesis gas as well as U.S. Pat. No. 6,685,754 to Kindig et al., the disclosures of which are incorporated herein by reference.

The acetic acid may be vaporized at the reaction temperature, and then it can be fed along with hydrogen in an undiluted state or diluted with a relatively inert carrier gas, such as nitrogen, argon, helium, carbon dioxide and the like.

Alternatively, acetic acid in vapor form may be taken directly as crude product from the flash vessel of a methanol carbonylation unit of the class described in U.S. Pat. No. 6,657,078 to Scates et al., the disclosure of which is incorporated herein by reference. The crude vapor product may be fed directly to the reaction zones of the present invention without the need for condensing the acetic acid and light ends or removing water, saving overall processing costs.

Contact or residence time can also vary widely, depending upon such variables as the amount of acetic acid, catalyst, reactor, temperature and pressure. Typical contact times range from a fraction of a second to more than several hours when a catalyst system other than a fixed bed is used, with preferred contact times, at least for vapor phase reactions, between about 0.5 and 100 seconds.

Typically, the catalyst is employed in a fixed bed reactor e.g. in the shape of an elongated pipe or tube where the reactants, typically in the vapor form, are passed over or through the catalyst. Other reactors, such as fluid or ebullient bed reactors, can be employed, if desired. In some instances, it is advantageous to use the hydrogenation catalysts in conjunction with an inert material to regulate the pressure drop, flow, heat balance or other process parameters in the catalyst bed including the contact time of the reactant compounds with the catalyst particles.

In one of the preferred embodiments there is also provided a process for selective and direct formation of ethyl acetate from acetic acid comprising: contacting a feed stream containing acetic acid and hydrogen at an elevated temperature with a suitable hydrogenating catalyst containing about 0.5 weight percent to about 1 weight percent of platinum or palladium and about 2.5 weight percent to about 5 weight percent of copper or cobalt on a suitable catalyst support. The preferred catalyst support is either silica or H-ZSM-5.

In this embodiment of the process of this invention, the preferred hydrogenation catalyst contains about one (1) weight percent platinum and about five (5) weight percent copper or about one (1) weight percent palladium and about five (5) weight percent cobalt. It is preferred that the hydrogenation catalysts are layered in a fixed bed and the reaction is carried out in the vapor phase using a feed stream of acetic acid and hydrogen in the molar range of about 1:20 to 1:5 and at a temperature in the range of about 225° C. to 275° C. and at a pressure of reaction zones in the range of about 8 to 20 atmospheres absolute, and the contact time of reactants is in the range of about 0.5 and 100 seconds.

Step (b): Enriching of Ethyl Acetate in the First Gaseous Product Stream

In the second step of the process of this invention, the ethyl acetate formed in the first reaction zone, step (a) of the process of this invention as described herein is further enriched so as to result in a stream containing at least 50 mole percent of ethyl acetate. Any of the methods known in the art can be employed for this purpose. For example, one can employ a suitable distillation column to remove the volatile gaseous byproducts at the overhead and the bottom column to separate the high boiling fractions. Various other cryogenic methods and/or temperature controlled trapping devices can also be employed, such as a scrubber to remove either the impurities or other byproducts having either low or high boiling points such that the resulting stream contained at least 50 mole percent of ethyl acetate.

Preferably the enriched product stream from the first reaction zone contained at least 60 mole percent of ethyl acetate. More preferably the enriched gaseous product stream from the first reaction zone contained at least 70 mole percent of ethyl acetate. Even more preferably the enriched gaseous product stream from the first reaction zone contained at least 80 mole percent of ethyl acetate.

Step (c): Cracking of Ethyl Acetate to Ethylene and Acetic Acid

The enriched gaseous product stream is then contacted in a second reaction zone at an elevated temperature with a cracking catalyst. Typically such cracking reactions are carried out at an elevated temperature in the range of about 300° C. to about 550° C. without any catalyst. The yields of ethylene and acetic acid can generally be high. See, for example, DePuy and King, *Chem. Rev.*, 60, 431-445 (1960), incorporated herein by reference in its entirety. However, such reactions can be catalyzed if desired utilizing a cracking catalyst. More importantly by the employment of a cracking catalyst in this step (b) of the process of this invention, it is possible to dramatically reduce the cracking temperature yet obtain high selectivity and conversions to cracking products.

Suitable cracking catalysts include sulfonic acid resins such as perfluorosulfonic acid resins disclosed in U.S. Pat. No. 4,399,305 to Schreck, noted above, the disclosure of which is incorporated herein by reference. Zeolites are also suitable as cracking catalysts as noted in U.S. Pat. No. 4,620,050 to Cognion et al, the disclosure of which is also incorporated herein by reference. Thus, a zeolite catalyst may be used to concurrently support a hydrogenating catalyst as described hereinabove and then to crack the resulting ethyl acetate to form ethylene and acetic acid.

Thus in accordance with one aspect of the process of this invention there is also provided a consolidated fixed bed reactor wherein the front end of the reactor is loaded with the hydrogenation catalyst as described hereinabove and the rear end of the reactor is loaded with a suitable cracking catalyst as described hereinabove thereby both steps (a) and (b) of the process of this invention can effectively be carried out in a single stage. Any of the known fixed bed reactors that can bring about such results can be employed for this purpose. Preferably a tubular reactor designed to contain two different catalyst layers as described herein is employed to achieve this task.

Typically, cracking of ethyl acetate in the presence of a cracking catalyst can be carried out in the temperature range of from about 150° C. to about 300° C., preferably in the range of from about 160° C. to about 250° C. and more preferably in the range of from about 170° C. to 225° C. Again, as described above, any of the zeolites can be used as cracking catalyst. Preferably, the cracking is carried out in the presence of a zeolite having a pore diameter above about 0.6 nm. Specific examples of such zeolites include, without any limitation, mordenites, zeolite X and zeolite Y as described herein.

As noted above, another preferred cracking catalyst that can be employed in step (c) of the process of this invention is perfluorosulfonic acid resin, which is commercially available under the trademark NAFION® from the duPont de Nemours Company at Wilmington, Del. Suitable variations of these resins are described in U.S. Pat. No. 4,065,512 to Cares and in duPont "Innovation," Volume 4, number 3, Spring 1973.

Step (d): Formation of VAM from the Second Gaseous Product Stream Containing Ethylene and Acetic Acid In a third reactor zone, the gaseous product stream from the cracking reactor is contacted further with a catalyst and a second feed containing molecular oxygen and optionally additional amount of acetic acid, if desired, in order to balance the stoichiometry of the reaction. It is preferable that equal mole ratio of ethylene and acetic acid is fed into the third reactor zone.

Any of the known catalysts for oxidative reaction of ethylene with acetic acid to form VAM can be employed in step (d) of the process of this invention, for example, as described in GB 1 559 540; U.S. Pat. Nos. 5,185,308; 5,691,267; 6,114,571; and WO 99/08791, the equivalent to U.S. Pat. No. 6,603,038. EP-A 0 330 853 describes impregnated catalysts for the production of VAM containing palladium, potassium, manganese and cadmium as additional promoter instead of gold. All of the references mentioned herein are incorporated herein by reference in their entirety.

GB 1 559 540 describes suitable catalysts that can be employed in the preparation of VAM by the reaction of ethylene, acetic acid and oxygen, as used in step (d) of the process of this invention. The catalyst is comprised of: (1) a catalyst support having a particle diameter of from 3 to 7 mm and a pore volume of from about 0.2 to 1.5 ml/g, a 10% by weight water suspension of the catalyst support having a pH from about 3.0 to 9.0, (2) a palladium-gold alloy distributed in a surface layer of the catalyst support, the surface layer extending less than 0.5 mm from the surface of the support, the palladium in the alloy being present in an amount of from about 1.5 to 5.0 grams per liter of catalyst, and the gold being present in an amount of from about 0.5 to 2.25 grams per liter of catalyst, and (3) from 5 to 60 grams per liter of catalyst of alkali metal acetate.

U.S. Pat. No. 5,185,308 describes a shell impregnated catalyst active for the production of VAM from ethylene, acetic acid and an oxygen containing gas, the catalyst consisting essentially of (1) a catalyst support having a particle diameter from about 3 to about 7 mm and a pore volume of 0.2 to 1.5 ml per gram, (2) palladium and gold distributed in the outermost 1.0 mm thick layer of the catalyst support particles, and (3) from about 3.5 to about 9.5% by weight of potassium acetate wherein the gold to palladium weight ratio in said catalyst is in the range 0.6 to 1.25.

U.S. Pat. No. 5,691,267 to Nicolau et al. describes a two step gold addition method for making a catalyst used in the gas phase formation of VAM from the reaction of ethylene, oxygen, and acetic acid. The catalyst is formed by (1) impregnating a catalyst carrier with aqueous solutions of a water-soluble palladium salt and a first amount of a water-soluble gold compound such as sodium-palladium chloride and auric chloride, (2) fixing the precious metals on the carrier by precipitating the water-insoluble palladium and gold compounds by treatment of the impregnated carriers with a reactive basic solution such as aqueous sodium hydroxide which reacts with the palladium and gold compounds to form hydroxides of palladium and gold on the carrier surface, (3) washing with water to remove the chloride ion (or other anion), and (4) reducing all the precious metal hydroxides to free palladium and gold, wherein the improvement comprises (5) impregnating the carrier with a second amount of a water-soluble gold compound subsequent to fixing a first amount of water-soluble gold agent, and (6) fixing the second amount of a water-soluble gold compound.

U.S. Pat. No. 6,114,571 to Abel et al. describes a catalyst for forming vinyl acetate in the gas phase from ethylene, acetic acid, and oxygen or oxygen-containing gases wherein the catalyst is comprised of palladium, gold, boron, and alkali metal compounds on a support. The catalyst is prepared by a) impregnating the support with soluble palladium and gold compounds; b) converting the soluble palladium and gold compounds on the support into insoluble compounds by means of an alkaline solution; c) reducing the insoluble palladium and gold compounds on the support by means of a reducing agent in the liquid phase; d) washing and subsequently drying the support; e) impregnating the support with a soluble alkali metal compound; and f) finally drying the support at a maximum of 150° C., wherein boron or boron compounds are applied to the catalyst prior to the final drying.

WO 99/08791, the equivalent of U.S. Pat. No. 6,603,038 to Hagemeyer et al., describes a method for producing catalysts containing metal nanoparticles on a porous support, especially for gas phase oxidation of ethylene and acetic acid to form VAM. The invention relates to a method for producing a catalyst containing one or several metals from the group of metals comprising the sub-groups Ib and VIIIb of the periodic table on porous support particles, characterized by a first step in which one or several precursors from the group of compounds of metals from sub-groups Ib and VIIIb of the periodic table is or are applied to a porous support, and a second step in which the porous, preferably nanoporous support to which at least one precursor has been applied is treated with at least one reduction agent, to obtain the metal nanoparticles produced in situ in the pores of said support.

Typically, step (d) of the process of the present invention is carried out heterogeneously with the reactants being present in the gas phase.

The molecular oxygen-containing gas used in step (d) of the process of the present invention may comprise other inert gases such as nitrogen. Preferably, molecular oxygen used in step (d) of the process of the present invention is air.

Step (d) of the process of the present invention may suitably be carried out at a temperature in the range of from about 140° C. to 220° C. and a pressure in the range of from about 1 to 100 atmospheres absolute. Step (d) of the process of the present invention can be carried out in any suitable reactor design capable of removing the heat of reaction in an appropriate way; preferred technical solutions are fixed or fluidized bed reactors as described herein.

Acetic acid conversions in the range of about 5 to 50% may be achieved in step (d) of the process of the present invention. Oxygen conversions in the range of about 20 to 100% may be achieved in step (d) of the present invention. In step (d) of the process of the present invention, the catalyst suitably has a productivity (space time yield, STY) in the range of about 100 to 2000 grams of vinyl acetate per hour per liter of catalyst, but >10,000 grams of vinyl acetate per hour per liter of catalyst is also suitable.

As already noted above, the third gaseous product stream from step (d) of the process comprises VAM and water and optionally also unreacted acetic acid, ethylene, ethyl acetate, ethane, nitrogen, carbon monoxide, carbon dioxide and possibly traces of other byproducts. Intermediate between step (d) and step (e) of the process of the invention it is preferred to remove ethylene, and ethane, carbon monoxide and carbon dioxide, if any, from the third product stream, suitably as an overhead gaseous fraction from a scrubbing column, in which a liquid fraction comprising vinyl acetate, water and acetic acid is removed from the base.

The third product stream from step (d) comprising VAM, water and acetic acid, with or without the intermediate scrubbing step, is separated in step (e) by distillation into an overhead azeotrope fraction comprising vinyl acetate and water and a base fraction comprising acetic acid.

VAM is recovered from the azeotrope fraction separated in step (d), suitably for example by decantation. The recovered VAM may, if desired, be further purified in a known manner. The base fraction comprising acetic acid separated in step (d) is preferably recycled, with or preferably without further purification, to step (a) or, if desired, to step (d) of the process.

The following Examples A-V describe the procedures used for the preparation of various catalysts employed in the Examples 1-15 which follow:

EXAMPLE A

Preparation of 1 Weight Percent Platinum and 5 Weight Percent Copper on High Purity Low Surface Area Silica Powdered and meshed high purity low surface area silica (94 g) of uniform particle size distribution of about 0.2 mm is dried at 120° C. in an oven under nitrogen atmosphere overnight and then cooled to room temperature. To this is added a solution of platinum nitrate (Chempur) (1.64 g) in distilled water (16 ml). The resulting slurry is dried in an oven gradually heated to 110° C. (>2 hours, 10° C./min). The impregnated catalyst mixture is then calcined at 500° C. (6 hours, 1° C./min). To this calcined and cooled material is added a solution of copper nitrate trihydrate (Alfa Aesar) (19 g) in distilled water (19 ml). The resulting slurry is dried in an oven gradually heated to 110° C. (>2 hours, 10° C./min). The impregnated catalyst mixture is then calcined at 500° C. (6 hours, 1° C./min).

EXAMPLE B

Preparation of 1 Weight Percent Palladium and 5 Weight Percent Cobalt on High Purity Low Surface Area Silica Powdered and meshed high purity low surface area silica (94 g) of uniform particle size distribution of about 0.2 mm is dried at 120° C. in an oven under nitrogen atmosphere overnight and then cooled to room temperature. To this is added a solution of palladium nitrate (Heraeus) (2.17 g) in distilled water (22 ml). The resulting slurry is dried in an oven gradually heated to 110° C. (>2 hours, 10° C./min). The impregnated catalyst mixture is then calcined at 500° C. (6 hours, 1° C./min). To this calcined and cooled material is added a solution of cobalt nitrate hexahydrate (24.7 g) in distilled water (25 ml). The resulting slurry is then dried in an oven gradually heated to 110° C. (>2 hours, 10° C./min). The impregnated catalyst mixture is then calcined at 500° C. (6 hours, 1° C./min).

EXAMPLE C

Preparation of 1 Weight Percent Palladium and 5 Weight Percent Cobalt on H-ZSM-5

The procedures of Example B are substantially repeated except for utilizing H-ZSM-5 as the catalyst support.

EXAMPLE D

Preparation of 5 Weight Percent Copper and 5 Weight Percent Chromium on High Purity Low Surface Area Silica Powdered and meshed high purity low surface area silica (90 g) of uniform particle size distribution of about 0.2 mm is dried at 120° C. in an oven under nitrogen atmosphere overnight and then cooled to room temperature. To this is added a solution of copper nitrate trihydrate (Alfa Aesar) (19 g) in distilled water (19 ml). The resulting slurry is then dried in an oven gradually heated to 110° C. (>2 hours, 10° C./min). The impregnated catalyst mixture is then calcined at 500° C. (6 hours, 1° C./min). To this calcined and cooled material is added a solution of chromium nitrate nonahydrate (Alfa Aesar) (32.5 g) in distilled water (65 ml). The resulting slurry is dried in an oven gradually heated to 110° C. (>2 hours, 10° C./min). The impregnated catalyst mixture is then calcined at 500° C. (6 hours, 1° C./min).

EXAMPLE E

Preparation of 5 Weight Percent Molybdenum Carbide ($MoC_2$) on High Purity Low Surface Area Silica Powdered and meshed high purity low surface area silica (95 g) of uniform particle size distribution of about 0.2 mm is dried at 120° C. in an oven under nitrogen atmosphere overnight and then cooled to room temperature. To this is added a solution of ammonium heptamolybdate hexahydrate (Sigma) (9.5 g) in distilled water (63 ml). The resulting slurry is dried in an oven gradually heated to 110° C. (>2 hours, 10° C./min). The impregnated catalyst mixture is then calcined at 500° C. (6 hours, 1° C./min). This results in molybdenum oxide on silica. It is then treated in a flow of methane at 500° C. to afford the titled catalyst.

EXAMPLE F

Preparation of 1 Weight Percent Platinum and 5 Weight Percent Molybdenum on Titania Powdered and meshed titania (94 g) of uniform particle size distribution of about 0.2 mm was dried at 120° C. in an oven under nitrogen atmosphere overnight and then cooled to room temperature. To this is added a solution of platinum nitrate (Chempur) (1.64 g) in distilled water (16 ml). The resulting slurry is dried in an oven gradually heated to 110° C. (>2 hours, 10° C./min). The impregnated catalyst mixture is then calcined at 500° C. (6 hours, 1° C./min). To this calcined and cooled material was added a solution of ammonium heptamolybdate hexahydrate (Sigma) (9.5 g) in distilled water (63 ml). The resulting slurry is dried in an oven gradually heated to 110° C. (>2 hours, 10° C./min). The impregnated catalyst mixture is then calcined at 500° C. (6 hours, 1° C./min).

EXAMPLE G

Preparation of 1 Weight Percent Palladium on High Purity Low Surface Area Silica Powdered and meshed high purity low surface area silica (99 g) of uniform particle size distribution of about 0.2 mm is dried at 120° C. in an oven under nitrogen atmosphere overnight and then cooled to room temperature. To this is added a solution of palladium nitrate (Heraeus) (2.17 g) in distilled water (22 ml). The resulting slurry is dried in an oven gradually heated to 110° C. (>2 hours, 10° C./min). The impregnated catalyst mixture is then calcined at 500° C. (6 hours, 1° C./min).

EXAMPLE H

Preparation of 1 Weight Percent Palladium and 5 Weight Percent Molybdenum on H-ZSM-5

The procedures of Example A are substantially repeated except for utilizing a solution of palladium nitrate (Heraeus) (2.17 g) in distilled water (22 ml), a solution of ammonium heptamolybdate hexahydrate (Sigma) (9.5 g) in distilled water (65 ml) and 94 grams of H-ZSM-5. The catalyst is sequentially impregnated first with molybdenum and then with palladium.

EXAMPLE I

Preparation of 1 Weight Percent Nickel and 5 Weight Percent Molybdenum on Carbon The procedures of Example A are substantially repeated except for utilizing a solution of nickel nitrate hexahydrate (Alfa Aesar) (4.96 g) in distilled water (5 ml), a solution of ammonium heptamolybdate hexahydrate (Sigma) (9.5 g) in distilled water (65 ml) and 94 grams of carbon. The catalyst is sequentially impregnated first with molybdenum and then with nickel.

EXAMPLE J

Preparation of 1 Weight Percent Platinum on Titania

The procedures of Example A are substantially repeated except for utilizing a solution of platinum nitrate (Chempur) (1.64 g) in distilled water (16 ml) and 99 grams of titania.

EXAMPLE K

Preparation of 1 Weight Percent Palladium and 5 Weight Percent Rhenium on Titania The procedures of Example A are substantially repeated except for utilizing a solution of palladium nitrate (Heraeus) (2.17 g) in distilled water (22 ml), a solution of perrhenic acid (7 g) in distilled water (14 ml) and 94 grams of titania. The catalyst is sequentially impregnated first with rhenium and then with palladium.

EXAMPLE L

Preparation of 1 Weight Percent Platinum and 5 Weight Percent Molybdenum on Carbon The procedures of Example F are substantially repeated except for utilizing 94 grams of carbon.

EXAMPLE M

Preparation of 1 Weight Percent Palladium and 5 Weight Percent Zirconium on Silica The procedures of Example A are substantially repeated except for utilizing a solution of palladium nitrate (Heraeus) (2.17 g) in distilled water (22 ml), a solution of zirconium nitrate pentahydrate (23.5 g) in distilled water (100 ml) and 94 grams of silica. The catalyst is sequentially impregnated first with zirconium and then with palladium.

EXAMPLE N

Preparation of 1 Weight Percent Platinum and 5 Weight Percent Copper on Titania

The procedures of Example A are substantially repeated except for utilizing 94 grams of titania.

EXAMPLE O

Preparation of 1 Weight Percent Nickel and 5 Weight Percent Rhenium on Titania

The procedures of Example A are substantially repeated except for utilizing a solution of nickel nitrate hexahydrate (Alfa Aesar) (4.96 g) in distilled water (5 ml), a solution of perrhenic acid (7 g) in distilled water (14 ml) and 94 grams of titania. The catalyst is sequentially impregnated first with rhenium and then with nickel.

EXAMPLE P

Preparation of 1 Weight Percent Platinum and 5 Weight Percent Molybdenum on Silica The procedures of Example F are substantially repeated except for utilizing 94 grams of silica.

EXAMPLE Q

Preparation of 1 Weight Percent Palladium and 5 Weight Percent Molybdenum on Silica The procedures of Example H are substantially repeated except for utilizing 94 grams of silica.

EXAMPLE R

Preparation of 5 Weight Percent Copper and 5 Weight Percent Zirconium on Silica

The procedures of Example A are substantially repeated except for utilizing a solution of copper nitrate trihydrate (Alfa Aesar) (19 g) in distilled water (19 ml), a solution of zirconium nitrate pentahydrate (23.5 g) in distilled water (100 ml) and 94 grams of silica. The catalyst is sequentially impregnated first with copper and then with zirconium.

EXAMPLE S

Preparation of K, Pd, Au/$TiO_2$

The title catalyst is prepared in accordance with the procedures set forth in U.S. Pat. No. 6,852,877 to Zeyss et al.

EXAMPLE T

Preparation of Pd and Au

A vinyl acetate catalyst containing Pd and Au for converting a stream of gas containing ethylene, oxygen or air, and acetic acid into VAM is prepared generally as follows:

The catalyst is prepared on spherical silica supports with diameters of about 5 mm. The silica supports are impregnated with an aqueous solution containing sodium palladium tetrachlorate and sodium tetracholroaurate in sufficient amounts such that the catalysts would have about 7 gm/l of palladium metal and about 7 gm/l of gold metal each.

After impregnation, the carrier is placed in a roto-evaporator, without vacuum, and treated with 283 ml of a 50% w/w aqueous solution of sodium hydroxide. The supports are rotated at about 5 rpm for about 2.5 hours in a sodium hydroxide solution at a temperature of 70° C. by rotation in a hot water bath. The resulting catalysts are reduced in a gas blend of 5% ethylene in nitrogen for about 5 hours at a temperature of about 150° C. at a flow rate of about 0.5 SCFH (standard cubic feet per hour) at atmospheric pressure to reduce the metal salts to metal.

The catalysts are then impregnated again with an aqueous solution of sodium tetrachloroaurate and 1.65 gm of a 50% w/w aqueous sodium hydroxide fixing solution. The resulting catalysts are reduced in a gas blend of 5% ethylene in nitrogen for about 5 hours at a temperature of about 150° C. at a flow rate of about 0.5 SCFH (standard cubic feet per hour) at atmospheric pressure to reduce the gold salts to gold metal.

EXAMPLE U

Preparation of Pd, Au, and K

A catalyst for preparing vinyl acetate in the gas phase from ethylene, acetic acid, and oxygen or oxygen-containing gases wherein the catalyst is prepared generally as follows:

250 ml of silicon dioxide catalyst sphere supports having a diameter of 7.3 mm are impregnated with 85 ml of an aqueous solution containing 4.6 g of $Na_2PdCl_4$ and 1.4 g of $NaAuCl_4$. The precipitation of the insoluble metal compounds is achieved by the addition of 283 ml of an aqueous solution of 17 g of borax. The vessel is then immediately rotated by means of a rotary evaporator, without vacuum, for 2.5 hours at 5 revolutions per minute (rpm). The reduction is achieved by the addition of 7 ml of hydrazine hydrate in 20 ml of water and immediate rotation of the vessel at 5 rpm for 1 hour.

The pellets thus obtained are dried for 1 hour at 1000° C. The reduced catalyst is impregnated with an aqueous solution containing 10 g of potassium acetate and having a volume corresponding to the absorption capacity of the dry support material. The catalyst is then dried again.

EXAMPLE V

Preparation of Pd, Au, and B

A catalyst containing nanosize metal particles on a porous support for the gas phase oxidation of ethylene and acetic acid to give vinyl acetate is prepared as follows:

200 g of $SiO_2$ supports having a BET surface area of 300 $m^2/g$ are sprayed discontinuously at a temperature of 30-32° C. with a hydrochloric acid solution of 3.33 g (18.8 mmol) of palladium chloride and 1.85 g (4.7 mmol) of auric acid in 500 ml of water over a period of 35 minutes in a coating unit.

The support spheres are subsequently dried and sprayed with 20 g of tripotassium citrate hydrate dissolved in 200 ml of water over a period of 25 minutes. At a drum rotation speed of 10 rpm, spraying is carried out discontinuously at 1 bar. The inlet temperature (warm air temperature) is 60° C. and the product temperature was 32-30° C. This gave a homogeneously impregnated coated catalyst having a shell thickness of 400 μm. The diameter of the nanosize particles is determined by means of TEM. The mean particle diameter is 30 nm.

Gas Chromatographic (GC) Analysis of the Products

The analysis of the products was carried out by online GC. A three channel compact GC equipped with one flame ionization detector (FID) and 2 thermal conducting detectors (TCDs) was used to analyze the reactants and products. The front channel was equipped with an FID and a CP-Sil 5 (20 m)+WaxFFap (5 m) column and was used to quantify:

Acetaldehyde
Ethanol
Acetone
Methyl acetate
Vinyl acetate
Ethyl acetate
Acetic acid
Ethylene glycol diacetate
Ethylene glycol
Ethylidene diacetate
Paraldehyde The middle channel was equipped with a TCD and Porabond Q column and was used to quantify:

$CO_2$
Ethylene
Ethane

The back channel was equipped with a TCD and Molsieve 5A column and was used to quantify:

Helium
Hydrogen
Nitrogen
Methane
Carbon monoxide

Prior to reactions, the retention time of the different components was determined by spiking with individual compounds and the GCs were calibrated either with a calibration gas of known composition or with liquid solutions of known compositions. This allowed the determination of the response factors for the various components.

Examples 1-10 describe procedures for the hydrogenation of acetic acid to ethyl acetate as described in step (a) of the process of the present invention.

EXAMPLE 1

The catalyst utilized was 1 weight percent platinum and 5 weight percent copper on silica prepared in accordance with the procedure of Example A.

In a tubular reactor made of stainless steel, having an internal diameter of 30 mm and capable of being raised to a controlled temperature, there are arranged 50 ml of 1 weight percent platinum and 5 weight percent copper on silica. The length of the catalyst bed after charging was approximately about 70 mm. Prior to the reaction the catalyst was reduced in situ by heating at a rate of 2° C./min to a final temperature of 400° C. Then, 5 mol % hydrogen in nitrogen was introduced to the catalyst chamber at a gas hourly space velocity (GHSV) of 7500 $h^{-1}$. After reduction, the catalyst was cooled to reaction temperature of 275° C. by continuing the gas flow of 5 mol % hydrogen in nitrogen. Once the reaction temperature was stabilized at 275° C. the hydrogenation of acetic acid was begun as follows.

A feed liquid was comprised essentially of acetic acid. The reaction feed liquid was evaporated and charged to the reactor along with hydrogen and helium as a carrier gas with an average combined gas hourly space velocity (GHSV) of about 1250 $hr^{-1}$ at a temperature of about 275° C. and pressure of 15 bar. The resulting feed stream contained a mole percent of acetic acid from about 4.4% to about 13.8% and the mole percent of hydrogen from about 14% to about 77%. A portion of the vapor effluent was passed through a gas chromatograph for analysis of the contents of the effluents. The selectivity to ethyl acetate was 88.5% at a conversion of acetic acid of 37%.

EXAMPLE 2

The catalyst utilized was 1 weight percent palladium and 5 weight percent cobalt on silica prepared in accordance with the procedure of Example B.

The procedure as set forth in Example 1 was substantially repeated with an average combined gas hourly space velocity (GHSV) of 2,500 $hr^{-1}$ of the feed stream of the vaporized acetic acid and hydrogen ($H_2$ to acetic acid mole ratio of 5) at a temperature of 250° C. and pressure of 8 bar. A portion of the vapor effluent is passed through a gas chromatograph for analysis of the contents of the effluents. The acetic acid conversion was 26% and ethyl acetate selectivity was 91%.

EXAMPLE 3

The catalyst utilized was 1 weight percent palladium and 5 weight percent cobalt on H-ZSM-5 prepared in accordance with the procedure of Example C.

The procedure as set forth in Example 1 was substantially repeated with an average combined gas hourly space velocity (GHSV) of 2,500 $hr^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 18% and ethyl acetate selectivity was 93%.

EXAMPLE 4

The catalyst utilized was 1 weight percent palladium and 5 weight percent cobalt on H-ZSM-5 prepared in accordance with the procedure of Example C.

The procedure as set forth in Example 1 was substantially repeated with an average combined gas hourly space velocity (GHSV) of 10,000 hr$^{-1}$ of the feed stream of the vaporized acetic acid and hydrogen ($H_2$ to acetic acid mole ratio of 5) at a temperature of 250° C. and pressure of 1 bar. A portion of the vapor effluent is passed through a gas chromatograph for analysis of the contents of the effluents. The acetic acid conversion was 6% and ethyl acetate selectivity was 96%. The other products formed were ethane (1.8%) and ethanol (0.3%).

EXAMPLE 5

The catalyst utilized was 1 weight percent palladium and 5 weight percent molybdenum on H-ZSM-5 prepared in accordance with the procedure of Example H.

The procedure as set forth in Example 1 was substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 18% and ethyl acetate selectivity was 93%. The other products formed were ethane (4.3%) and ethanol (0.2%).

EXAMPLE 6

The catalyst utilized was 1 weight percent nickel and 5 weight percent molybdenum on carbon prepared in accordance with the procedure of Example I.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 6% and ethyl acetate selectivity was 88%. The other products formed were ethane (3.3%) and ethanol (4.9%).

EXAMPLE 7

The catalyst utilized was 1 weight percent platinum on titania prepared in accordance with the procedure of Example J.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 41% and ethyl acetate selectivity was 88%. The other products formed were ethane (4.8%) and methane (1.7%).

EXAMPLE 8

The catalyst utilized was the same catalyst used in Example 7 which was reused in this Example 8.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 41% and ethyl acetate selectivity was 87%. The other products formed were ethane (5%) and methane (1.7%).

EXAMPLE 9

The catalyst utilized was 1 weight percent palladium and 5 weight percent rhenium on titania prepared in accordance with the procedure of Example K.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 61% and ethyl acetate selectivity was 87%. The other products formed were ethanol (11%) and acetaldehyde (1.3%).

EXAMPLE 10A

The catalyst utilized was 1 weight percent platinum and 5 weight percent molybdenum on carbon prepared in accordance with the procedure of Example L.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 15% and ethyl acetate selectivity was 85%. The other products formed were ethane (7.1%) and ethanol (5.2%).

EXAMPLE 10B

The catalyst utilized was 1 weight percent palladium and 5 weight percent zirconium on silica prepared in accordance with the procedure of Example M.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 8.3% and ethyl acetate selectivity was 84%. The other products formed were methane (7.9%) and ethane (1%).

EXAMPLE 10C

The catalyst utilized was 1 weight percent platinum and 5 weight percent copper on titania prepared in accordance with the procedure of Example N.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 10% and ethyl acetate selectivity was 84%. The other products formed were acetone (8.4%) and acetaldehyde (7.1%).

EXAMPLE 10D

The catalyst utilized was 1 weight percent nickel and 5 weight percent rhenium on titania prepared in accordance with the procedure of Example O.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 16.2% and ethyl acetate selectivity was 83%. The other products formed were ethanol (10.4%) and ethane (2%).

EXAMPLE 10E

The catalyst utilized was 1 weight percent platinum and 5 weight percent molybdenum on silica prepared in accordance with the procedure of Example P.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 14.3% and ethyl acetate selectivity was 82.4%. The other products formed were ethane (6.6%) and ethanol (5.7%).

EXAMPLE 10F

The catalyst utilized was 1 weight percent palladium and 5 weight percent molybdenum on silica prepared in accordance with the procedure of Example Q.

The procedure as set forth in Example 1 is substantially repeated with an average combined gas hourly space velocity (GHSV) of 2,500 hr$^{-1}$ of the feed stream of the vaporized acetic acid and hydrogen (H2 to acetic acid mole ratio of 5) at a temperature of 250° C. and pressure of 15 bar. A portion of the vapor effluent is passed through a gas chromatograph for analysis of the contents of the effluents. The acetic acid conversion was 9.8% and ethyl acetate selectivity was 82%. The other products formed were ethanol (8.3%) and ethane (3.5%).

EXAMPLE 10G

The catalyst utilized was 5 weight percent copper and 5 weight percent zirconium on silica prepared in accordance with the procedure of Example R.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 2.2% and ethyl acetate selectivity was 81.4%. The other products formed were ethane (3.3%) and acetaldehyde (10%).

EXAMPLE 10H

The catalyst utilized was 5 weight percent copper and 5 weight percent chromium on silica prepared in accordance with the procedure of Example D.

The procedure as set forth in Example 1 is substantially repeated with an average combined gas hourly space velocity (GHSV) of 2,500 hr$^{-1}$ of the feed stream of the vaporized acetic acid and hydrogen at a temperature of 250° C. and pressure of 15 bar. A portion of the vapor effluent is passed through a gas chromatograph for analysis of the contents of the effluents. The acetic acid conversion is 25% and ethyl acetate selectivity is about 75%.

EXAMPLE 10I

The catalyst utilized was 5 weight percent molybdenum carbide ($MOC_2$) on High Purity Low Surface Area Silica prepared in accordance with the procedure of Example E.

The procedure as set forth in Example 1 is substantially repeated with an average combined gas hourly space velocity (GHSV) of 2,500 hr$^{-1}$ of the feed stream of the vaporized acetic acid and hydrogen at a temperature of 250° C. and pressure of 15 bar. A portion of the vapor effluent is passed through a gas chromatograph for analysis of the contents of the effluents. The acetic acid conversion is 25% and ethyl acetate selectivity is 75%.

EXAMPLE 10J

The catalyst utilized was 1 weight percent platinum and 5 weight percent molybdenum on titania prepared in accordance with the procedure of Example F.

The procedure as set forth in Example 1 is substantially repeated with an average combined gas hourly space velocity (GHSV) of 2,500 hr$^{-1}$ of the feed stream of the vaporized acetic acid and hydrogen at a temperature of 250° C. and pressure of 15 bar. A portion of the vapor effluent is passed through a gas chromatograph for analysis of the contents of the effluents. The acetic acid conversion is about 50% and ethyl acetate selectivity is 85%.

EXAMPLE 10K

The catalyst utilized was 1 weight percent palladium on silica prepared in accordance with the procedure of Example G.

The procedure as set forth in Example 1 is substantially repeated with an average combined gas hourly space velocity (GHSV) of 2,500 hr$^{-1}$ of the feed stream of the vaporized acetic acid and hydrogen at a temperature of 250° C. and pressure of 15 bar. A portion of the vapor effluent is passed through a gas chromatograph for analysis of the contents of the effluents. The acetic acid conversion is about 65% and ethyl acetate selectivity is 85%.

Example 11 describes cracking of ethyl acetate to ethylene and acetic acid as described in step (b) of the present invention.

EXAMPLE 11

The procedure as set forth in U.S. Pat. No. 4,399,305 to Schreck is used to crack ethyl acetate to ethylene and acetic acid using NAFION as the cracking catalyst at 185° C. in step (c) of the process of the present invention using the ethyl acetate enriched feed stream from step (b) of the process of the present invention.

EXAMPLE 12

The catalyst utilized is K, Pd, Au/TiO$_2$ prepared in accordance with the procedure of Example S. The procedure as set forth in U.S. Pat. No. 6,852,877 to Zeyess et al. is used to carry out step (d) of the process of the present invention using the feed stream from step (c) of the process of the present invention and molecular oxygen in combination with additional amounts of acetic acid, if desired, to balance the stoichiometry of the product stream.

EXAMPLE 13

The catalyst utilized is Pd and Au prepared in accordance with the procedure of Example T. The procedure as set forth in U. S. Patent No. 5,691,267 to Nicolau et al. is used to carry out step (d) of the process of the present invention using the feed stream from step (c) of the process of the present invention and molecular oxygen in combination with additional amounts of acetic acid, if desired, to balance the stoichiometry of the product stream.

EXAMPLE 14

The catalyst utilized is Pd, Au, and K prepared in accordance with the procedure of Example U. The procedure as set forth in U. S. Patent No. 6,114,571 to Abel et al. is used to carry out step (d) of the process of the present invention using the feed stream from step (c) of the process of the present invention and molecular oxygen in combination with additional amounts of acetic acid, if desired, to balance the stoichiometry of the product stream.

EXAMPLE 15

The catalyst utilized is Pd, Au, and B prepared in accordance with the procedure of Example S. The procedure as set forth in U. S. Patent No. 6,603,038 to Hagemeyer et al. is used to carry out step (d) of the process of the present invention using the feed stream from step (c) of the process of the present invention and molecular oxygen in combination with additional amounts of acetic acid, if desired, to balance the stoichiometry of the product stream.

While the invention has been illustrated in connection with particular examples, modifications to these examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. A process for the production of vinyl acetate from acetic acid comprising:
   a. contacting a feed stream containing acetic acid and hydrogen at an elevated temperature with a suitable hydrogenation catalyst consisting essentially of at least one metal selected from the group consisting of nickel, platinum and palladium and at least one metal selected from copper and cobalt supported on a catalyst support selected from the group consisting of H-ZSM-5, silica, alumina, silica-alumina, calcium silicate, carbon, and mixtures thereof; to form a first gaseous product stream comprising ethyl acetate
   b. enriching said first gaseous product stream with ethyl acetate to at least 50 mole percent;
   c. contacting in a second reaction zone said enriched first gaseous product stream obtained in step (b) at an elevated temperature with a suitable cracking catalyst to form a second gaseous product comprising a mixture of ethylene and acetic acid;
   d. contacting in a third reaction zone said second gaseous product obtained in step (c) in combination with a second feed stream comprising molecular oxygen and optionally additional amounts of acetic acid in the presence of a catalyst to form a third gaseous product stream comprising vinyl acetate; and
   e. separating the vinyl acetate from said third gaseous product stream.

2. The process according to claim 1, wherein the hydrogenating catalyst metal in step (a) is selected from the group consisting of a combination of platinum and copper; and a combination of palladium and cobalt at a weight ratio in the range of about 0.1 to about 1.

3. The process according to claim 1, wherein the cracking catalyst in step (c) is selected from the group consisting of perfluorosulfonic acid resin, H-mordenite, ZSM-5, zeolite X, and zeolite Y.

4. The process according to claim 1, wherein the first gaseous product stream is enriched with ethyl acetate at least up to 80 mole percent in step (b).

5. The process according to claim 1, wherein the reactants in step (a) consist of acetic acid and hydrogen with a molar ratio in the range of about 100:1 to 1:100, the temperature of the reaction zones are in the range of about 200° C. to 300° C., and the pressure of the reaction zones are in the range of about 1 to 30 atmospheres absolute.

6. The process according to claim 1, wherein the reactants in step (a) consist of acetic acid and hydrogen with a molar ratio in the range of about 1:20 to 1:2, the temperature of the reaction zones are in the range of about 225° C. to 275° C., and the pressure of the reaction zones are in the range of about 1 to 30 atmospheres absolute.

7. The process according to claim 1, wherein the hydrogenation catalyst in step (a) consists essentially of platinum supported on a catalyst support with a loading of about 0.5 weight percent to about 1 weight percent and copper supported on the catalyst support with a loading of about 2.5 weight percent to about 5 weight percent and wherein the catalyst support is chosen from the group consisting of silica, silica-alumina; and combinations thereof.

8. The process according to claim 1, wherein the hydrogenation catalyst in step (a) consists essentially of palladium supported on a catalyst support with a loading of about 1 weight percent and cobalt supported on a catalyst support with a loading of about 5 weight percent and wherein the catalyst support is silica, silica-alumina, and combinations thereof.

9. The process according to claim 1, wherein the catalyst in step (d) comprises palladium.

10. The process according to claim 9, wherein the catalyst in step (d) further comprises gold and potassium acetate.

11. The process according to claim 9, wherein the palladium is supported on a catalyst support selected from the group consisting of silica, alumina, silica-alumina, zirconia and combinations thereof.

12. The process according to claim 1, wherein the mole ratio of ethylene to molecular oxygen is about 4:1 or less.

13. The process according to claim 1, wherein acetic acid is supplied to step (a) in the form of vapor comprising uncondensed acetic acid, light ends and water from a methanol carbonylation unit.

14. A process for the production of vinyl acetate from acetic acid comprising:
   a. contacting in a first reaction zone a feed stream containing acetic acid and hydrogen at an elevated temperature with a suitable hydrogenating catalyst to form a first gaseous product containing ethyl acetate, said hydrogenating catalyst being disposed on a catalyst support selected from the group consisting of H-ZSM-5, silica, alumina, silica-alumina, calcium silicate, carbon, and mixtures thereof, and consisting essentially of a first metal chosen from the group consisting of:
      i. about 0.5 weight percent to about 1 weight percent of platinum;
      ii. about 0.5 weight percent to about 1 weight palladium; and
      iii. combinations thereof; and
      a second metal chosen from the group consisting of:
      i. 2.5 weight percent to about 5 weight percent of copper;
      ii. 2.5 weight percent to about 5 weight percent cobalt; and
      iii. combinations thereof.
   b. enriching said first gaseous product stream with ethyl acetate to at least 50 mole percent;
   c. contacting in a second reaction zone said enriched first gaseous product obtained in step (b) at an elevated temperature with a cracking catalyst chosen from perfluorosulfonic acid resin, H-mordenite or ZSM-5, to form a second gaseous product comprising a mixture of ethylene and acetic acid;
   d. contacting in a third reaction zone said gaseous product stream obtained in step (c) in combination with a second feed stream comprising molecular oxygen and optionally additional amounts of acetic acid in the presence of a catalyst to form a second gaseous product stream comprising vinyl acetate; and
   e. separating the vinyl acetate from said second gaseous product stream.

15. The process according to claim 14, wherein the hydrogenation in step (a) is carried out over a hydrogenating catalyst on a support, which catalyst is selected from the group consisting of:
   i. platinum at a loading level of about 0.5 weight percent and copper at a loading level of about 2.5 weight percent supported on silica; and
   ii. platinum at a loading level of about 1 weight percent and copper at a loading level of about 5 weight percent supported on silica; and
   iii. palladium at a loading level of about one (1) weight percent and cobalt at a loading level of about 5 weight percent supported on silica.

16. The process according to claim 15, wherein the hydrogenation catalyst in step (a) is platinum at a loading level of about one (1) weight percent and copper at a loading level of about five (5) weight percent supported on silica.

17. The process according to claim 14 wherein the hydrogenating catalyst in step (a) is palladium at a loading level of about one (1) weight percent and cobalt at a loading level of about five (5) weight percent supported on silica.

18. The process according to claim 15 wherein the hydrogenation in step (a) is carried out at a pressure just sufficient to overcome the pressure drop across the catalytic bed.

19. The process according to claim 14, wherein the reactants in step (a) consist of acetic acid and hydrogen with a molar ratio in the range of about 100:1 to 1:100 the temperature of the reaction zones are in the range of about 200° C. to 300° C., and the pressure of the reaction zones are in the range of about 5 to 25 atmospheres absolute and the contact time of reactants and catalyst is in the range of about 0.5 to 100 seconds.

20. The process according to claim 14, wherein the reactants in step (a) consist of acetic acid and hydrogen with a molar ratio in the range of about 1:20 to 1:2, the temperature of the reaction zones are in the range of about 225° C. to 275° C., and the pressure of the reaction zones are in the range of about 8 to 20 atmospheres absolute and the contact time of reactants and catalyst is in the range of about 0.5 to 100 seconds.

21. The process according to claim 14, wherein the cracking catalyst in step (b) is perfluorosulfonic acid resin.

22. The process according to claim 14, wherein the catalyst in step (d) comprises palladium.

23. The process according to claim 22, wherein the catalyst in step (d) further comprises gold and potassium acetate.

24. The process according to claim 22, wherein the palladium is supported on a catalyst support selected from the group consisting of silica, alumina, silica-alumina, zirconia and combinations thereof.

25. The process according to claim 22, wherein the mole ratio of ethylene to molecular oxygen is about 4:1 or less.

26. The process according to claim 14, wherein acetic acid is supplied in the form of vapor comprising uncondensed acetic acid, light ends and water from a methanol carbonylation unit.

* * * * *